United States Patent
Kumar et al.

(10) Patent No.: US 10,006,877 B2
(45) Date of Patent: Jun. 26, 2018

(54) ROUTE EXAMINING SYSTEM AND METHOD

(71) Applicant: General Electric Company, Schenectady, NY (US)

(72) Inventors: Ajith Kuttannair Kumar, Erie, PA (US); Jeffrey Michael Fries, Grain Valley, MO (US); Joseph Forrest Noffsinger, Grain Valley, MO (US); Michael Scott Mitchell, Grain Valley, MO (US); Steven Joseph Ehret, Lawrence Park, PA (US)

(73) Assignee: General Electric Company, Schenectady, NY (US)

(*) Notice: Subject to any disclaimer, the term of this patent is extended or adjusted under 35 U.S.C. 154(b) by 236 days.

(21) Appl. No.: 14/464,473

(22) Filed: Aug. 20, 2014

(65) Prior Publication Data

US 2016/0054250 A1    Feb. 25, 2016

(51) Int. Cl.
*G01N 27/20*    (2006.01)
*B61L 3/00*    (2006.01)

(52) U.S. Cl.
CPC .................... *G01N 27/20* (2013.01)

(58) Field of Classification Search
CPC ...... B61L 23/044; B61L 23/045; B61L 3/121; B61L 25/026; B61L 25/025; B61L 23/34; B61L 3/00; B61L 3/004; B61L 3/12; G01M 5/0033; B61K 9/10; G01N 27/20; G01N 27/82; G01N 27/84; G01N 27/61; G01N 27/28; G01R 25/00
See application file for complete search history.

(56) References Cited

U.S. PATENT DOCUMENTS

| | | | |
|---|---|---|---|
| 3,505,742 A | 4/1970 | Fiechter | |
| 3,517,307 A | 6/1970 | Hronik et al. | |
| 3,604,359 A | 9/1971 | Doorley et al. | |
| 3,696,243 A * | 10/1972 | Risely | B61L 23/044 246/121 |
| 3,850,390 A | 11/1974 | Geiger | |
| 3,864,039 A | 2/1975 | Wilmarth | |
| 3,870,952 A | 3/1975 | Sibley | |

(Continued)

FOREIGN PATENT DOCUMENTS

| | | |
|---|---|---|
| EP | 0378781 A1 | 7/1990 |
| EP | 0953491 A1 | 11/1999 |

(Continued)

OTHER PUBLICATIONS

Australian Office Action & Examination report issued in connection with corresponding AU Application No. 2015215857 on Feb. 17, 2016.

(Continued)

*Primary Examiner* — Son Le
(74) *Attorney, Agent, or Firm* — GE Global Patent Operation; John A. Kramer

(57) ABSTRACT

A system may include a coded test signal transmission system configured to transmit a unique coded test signal along a route, and a coded test signal receiving system configured to receive the unique coded test signal along the route. The unique coded test signal received by the coded test signal receiving system is used to determine one or more characteristics of the route.

18 Claims, 4 Drawing Sheets

(56) References Cited

U.S. PATENT DOCUMENTS

| | | |
|---|---|---|
| 3,987,989 A | 10/1976 | Geiger |
| 4,005,601 A | 2/1977 | Botello |
| 4,117,529 A | 9/1978 | Stark et al. |
| 4,145,018 A | 3/1979 | Poggio et al. |
| 4,207,569 A | 6/1980 | Meyer |
| 4,259,018 A | 3/1981 | Poirier |
| 4,306,694 A | 12/1981 | Kuhn |
| 4,389,033 A | 6/1983 | Hardman |
| 4,417,522 A | 11/1983 | Theurer et al. |
| 4,430,615 A | 2/1984 | Calvert |
| 4,467,430 A | 8/1984 | Even et al. |
| 4,490,038 A | 12/1984 | Theurer et al. |
| 4,609,870 A | 9/1986 | Lale et al. |
| 4,654,973 A | 4/1987 | Worthy |
| 4,723,738 A | 2/1988 | Franke |
| 4,728,063 A | 3/1988 | Petit et al. |
| 4,735,384 A | 4/1988 | Elliott |
| 4,751,571 A | 6/1988 | Lillquist |
| 4,783,593 A | 11/1988 | Noble |
| 4,886,226 A | 12/1989 | Frielinghaus |
| 4,915,504 A | 4/1990 | Thurston |
| 4,979,392 A | 12/1990 | Guinon |
| 5,203,089 A | 4/1993 | Trefouel et al. |
| 5,275,051 A | 1/1994 | De Beer |
| 5,452,222 A | 9/1995 | Gray et al. |
| 5,628,479 A | 5/1997 | Ballinger |
| 5,680,054 A | 10/1997 | Gauthier |
| 5,698,977 A | 12/1997 | Simpson et al. |
| 5,751,144 A | 5/1998 | Weischedel |
| 5,769,364 A | 6/1998 | Cipollone |
| 6,011,901 A | 1/2000 | Kirsten |
| 6,088,635 A | 7/2000 | Cox et al. |
| 6,102,340 A | 8/2000 | Peek et al. |
| 6,128,558 A | 10/2000 | Kernwein |
| 6,262,573 B1 | 7/2001 | Wojnarowski et al. |
| 6,356,299 B1 | 3/2002 | Trosino et al. |
| 6,416,020 B1 | 7/2002 | Gronskov |
| 6,532,038 B1 | 3/2003 | Haring et al. |
| 6,540,180 B2 | 4/2003 | Anderson |
| 6,553,838 B2 | 4/2003 | Amini |
| 6,570,497 B2 | 5/2003 | Puckette et al. |
| 6,587,763 B2 * | 7/2003 | Ishikawa ............ B61L 27/0038 246/3 |
| 6,600,999 B2 | 7/2003 | Clark et al. |
| 6,647,891 B2 | 11/2003 | Holmes et al. |
| 6,655,639 B2 | 12/2003 | Grappone |
| 6,768,298 B2 | 7/2004 | Katragadda et al. |
| 6,778,284 B2 | 8/2004 | Casagrande |
| 6,779,761 B2 | 8/2004 | Holgate |
| 6,830,224 B2 | 12/2004 | Lewin et al. |
| 6,845,953 B2 | 1/2005 | Kane et al. |
| 6,951,132 B2 | 10/2005 | Davenport et al. |
| 6,964,202 B2 | 11/2005 | Buttle et al. |
| 6,995,556 B2 | 2/2006 | Nejikovsky et al. |
| 7,036,774 B2 | 5/2006 | Kane et al. |
| 7,226,021 B1 | 6/2007 | Anderson et al. |
| 7,268,565 B2 | 9/2007 | Anderson |
| 7,296,770 B2 | 11/2007 | Franke |
| 7,312,607 B2 | 12/2007 | Nygaard |
| 7,463,348 B2 | 12/2008 | Chung |
| 7,616,329 B2 | 11/2009 | Villar et al. |
| 7,823,841 B2 | 11/2010 | Anderson et al. |
| 7,845,504 B2 | 12/2010 | Davenport et al. |
| 7,938,370 B1 | 5/2011 | Lechevin et al. |
| 7,954,770 B2 | 6/2011 | Tomlinson, Jr. et al. |
| 7,965,312 B2 | 6/2011 | Chung et al. |
| 7,999,848 B2 | 8/2011 | Chew |
| 8,125,219 B2 | 2/2012 | Jungbluth et al. |
| 8,180,590 B2 | 5/2012 | Szwilski et al. |
| 8,233,662 B2 | 7/2012 | Bhotika et al. |
| 8,335,606 B2 | 12/2012 | Mian et al. |
| 8,405,837 B2 | 3/2013 | Nagle, II et al. |
| 8,412,393 B2 | 4/2013 | Anderson et al. |
| 8,599,005 B2 | 12/2013 | Fargas et al. |
| 8,712,610 B2 | 4/2014 | Kumar |
| 8,744,196 B2 | 6/2014 | Sharma et al. |
| 2002/0113170 A1 | 8/2002 | Grappone |
| 2002/0148931 A1 | 10/2002 | Anderson |
| 2003/0020469 A1 | 1/2003 | Katragadda et al. |
| 2003/0048193 A1 | 3/2003 | Puckette et al. |
| 2003/0070492 A1 | 4/2003 | Buttle et al. |
| 2003/0128030 A1 | 7/2003 | Hintze et al. |
| 2003/0142297 A1 | 7/2003 | Casagrande |
| 2004/0261533 A1 * | 12/2004 | Davenport ............ B61L 23/044 73/659 |
| 2005/0018748 A1 | 1/2005 | Ringermacher et al. |
| 2006/0017911 A1 | 1/2006 | Villar et al. |
| 2007/0132463 A1 | 6/2007 | Anderson |
| 2007/0145982 A1 | 6/2007 | Anderson et al. |
| 2008/0105791 A1 * | 5/2008 | Karg ................ B61K 9/10 246/120 |
| 2008/0296441 A1 | 12/2008 | Anderson et al. |
| 2010/0207620 A1 | 8/2010 | Gies |
| 2011/0216200 A1 | 9/2011 | Chung et al. |
| 2012/0192756 A1 | 8/2012 | Miller et al. |
| 2012/0300060 A1 | 11/2012 | Farritor |
| 2013/0191070 A1 | 7/2013 | Kainer et al. |
| 2013/0334373 A1 * | 12/2013 | Malone, Jr. ............ B61L 23/044 246/2 R |
| 2014/0138493 A1 | 5/2014 | Noffsinger et al. |

FOREIGN PATENT DOCUMENTS

| | | |
|---|---|---|
| EP | 1236634 A1 | 9/2002 |
| EP | 1600351 A1 | 11/2005 |
| WO | 2004001406 A1 | 12/2003 |
| WO | 2006065730 A2 | 6/2006 |
| WO | 2006112959 A2 | 10/2006 |
| WO | 2009087385 A2 | 7/2009 |

OTHER PUBLICATIONS

"Spread Spectrum, CDMA and GPS" http://alumni.cs.ucr.edu/~saha/stuff/cdma_gps.htm, pp. 10, Mar. 8, 2016.

Ha et al., "Study of Spread Spectrum Multiple Access for Satellite Communications with Overlay on Current Services", The Bradley Department of Electrical Engineering, pp. 1-236, Jan. 1, 1989.

Australian Examination Report issued in connection with corresponding AU Application No. 2015215857 dated Jan. 18, 2017.

* cited by examiner

ROUTE EXAMINING SYSTEM AND METHOD

TECHNICAL FIELD

Embodiments of the disclosure generally relate to examining routes traveled by vehicles.

BACKGROUND

Routes that are traveled by vehicles may become damaged over time with extended use. For example, tracks or rails on which rail vehicles travel may become damaged and/or broken. A variety of known systems are used to examine rail tracks to identify where the damaged and/or broken portions of the track are located. For example, some systems use cameras, lasers, and the like, to optically detect breaks and damage to the tracks. The cameras and lasers may be mounted on the rail vehicles, but they are generally expensive and may be difficult to be used in an industrial freight environment. As a result, the cameras and lasers may not be able to be used during regular operation (for example, travel) of the rail vehicles in revenue service.

Other systems use ultrasonic transducers that are placed at or near the tracks to ultrasonically inspect the tracks. These systems may require very slow movement of the transducers relative to the tracks in order to detect damage to the track. When a suspect location is found by an ultrasonic inspection vehicle, a follow-up manual inspection may be required for confirmation of defects using transducers that are manually positioned and moved along the track and/or are moved along the track by a relatively slower moving inspection vehicle. Inspections of the track can take a considerable amount of time, during which the inspected section of the route may be unusable by regular route traffic.

Other systems use human inspectors who move along the track to inspect for broken and/or damaged sections of track. This manual inspection is slow and prone to errors.

Other systems use wayside devices that send electric signals through the tracks. If the signals are not received by other wayside devices, then a circuit that includes the track is identified as being open and the track is considered to be broken. These systems are limited at least in that the wayside devices are immobile. As a result, the systems cannot inspect large spans of track and/or a large number of devices must be installed in order to inspect the large spans of track. These systems are also limited at least in that a single circuit could stretch for multiple miles. As a result, if the track is identified as being open and is considered broken, it is difficult and time-consuming to locate the exact location of the break within the long circuit. For example, a maintainer must patrol the length of the circuit to locate the problem.

These systems are also limited at least in that other track features, such as highway (for example, hard wire) crossing shunts, wide band (for example, capacitors) crossing shunts, narrow band (for example, tuned) crossing shunts, switches, insulated joints, and turnouts (for example, track switches) may emulate the signal response expected from a broken rail and provide a false alarm. For example, scrap metal on the track, crossing shunts, etc., may short the rails together, preventing the current from traversing the length of the circuit, indicating that the circuit is open. Additionally, insulated joints and/or turnouts may include intentional conductive breaks that create an open circuit. In response, the system may identify a potentially broken section of track, and a person or machine may be dispatched to patrol the circuit to locate the break, even if the detected break is a false alarm (for example, not a break in the track).

Further, some systems may be susceptible to interfering with other railroad systems. As an example, a system may transmit a signal into a track or rail. However, the transmitted signal may interfere with other vehicle systems or rail systems. Accordingly, the other systems may be adversely affected through signal interference.

BRIEF DESCRIPTION

In an embodiment, a system may include a coded test signal transmission system configured to transmit a unique coded test signal along a route, and a coded test signal receiving system configured to receive the unique coded test signal along the route. The unique coded test signal received by the coded test signal receiving system may be used to determine one or more characteristics of the route.

In one embodiment, the coded test signal transmission system is on or within a first vehicle, and the coded test signal receiving system is on or within a second vehicle that is separate and distinct from the first vehicle. In another embodiment, the coded test signal transmission system and the coded test signal receiving system are on the same vehicle. In yet another embodiment, one of the coded test signal transmission system or the coded test signal receiving system is on or within a vehicle, and the other of the coded test signal transmission system or the coded test signal receiving system is on or within a wayside device positioned on the route. Alternatively, one of the coded test signal transmission system or the coded test signal receiving system may be on or within a first wayside device positioned on the route, and the other of the coded test signal transmission system or the coded test signal receiving system may be on or within a second wayside device positioned on the route.

The coded test signal may include a chirp signal. The chirp signal may be transmitted over at least two frequencies during a period of time. The coded test signal receiving system may store coded data that is compared to the chirp signal received by the coded test signal receiving system.

The coded test signal receiving system may be configured to determine one or more undetectable frequencies. The coded test signal receiving system may be configured to communicate with the coded test signal transmission system to prevent the coded test signal transmission system from transmitting the coded test signal at the one or more undetectable frequencies.

One or both the coded test signal transmitting system and the coded test signal receiving system may be configured to determine one or more avoided frequencies that are used by other systems along the route. The coded test signal transmitting system may avoid transmitting the coded test signal using the one or more avoided frequencies.

In an embodiment, the coded test signal may include a spread spectrum chirping coded signal, which may include a random or pseudo-random signal. The coded test signal transmission system may be configured to switch the spread spectrum chirping coded signal between on and off states. The coded test signal transmission system may change the spread spectrum chirping coded signal each time the coded test signal transmission switches the spread spectrum chirping coded signal to the on state.

The coded test signal receiving system may determine that the route is damaged in response to the coded test signal that is received by the coded test signal receiving system failing to meet a matching threshold.

An embodiment provides a method that may include receiving a unique coded test signal transmitted by a coded test signal transmission system along a route at a coded test signal receiving system, and using the unique coded test signal received by the coded test signal receiving system to determine one or more characteristics of the route.

The receiving operation may include receiving the coded test signal as a chirp signal that is transmitted over at least two frequencies during a period of time. The method may include storing coded data at the coded test signal receiving system, and comparing the chirp signal received by the coded test signal receiving system to the coded data.

The method may include determining one or more undetectable frequencies, and preventing transmission of the coded test signal transmission system at the one or more undetectable frequencies.

The method may include determining one or more avoided frequencies that are used by other systems along the route, and avoiding transmission of the coded test signal using the one or more avoided frequencies.

In an embodiment, the receiving operation includes receiving the coded test signal as a spread spectrum chirping coded signal including a random signal. The method may include switching the spread spectrum chirping coded signal between on and off states, and changing the spread spectrum chirping coded signal each time the coded test signal transmission switches the spread spectrum chirping coded signal to the on state.

The using operation may include determining that the route is damaged in response to a received coded test signal failing to meet a matching threshold.

BRIEF DESCRIPTION OF THE DRAWINGS

Reference is made to the accompanying drawings in which particular embodiments and further benefits of the invention are illustrated as described in more detail in the description below, in which.

DETAILED DESCRIPTION

Figure 1A:
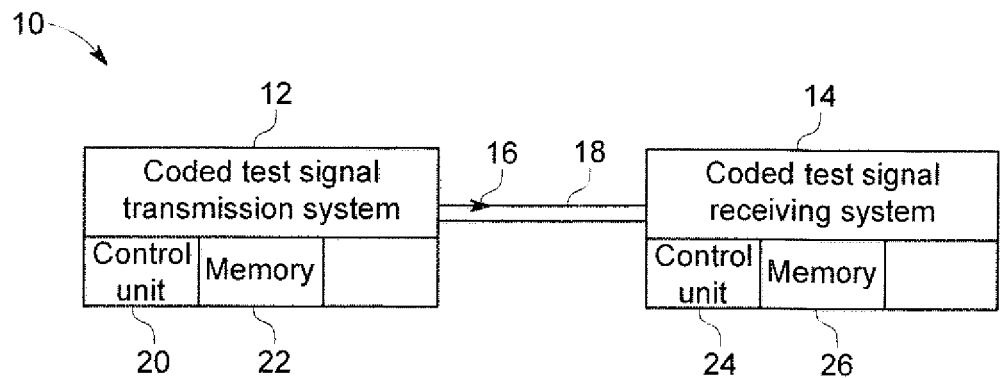
FIG. 1A illustrates a schematic diagram of a route examining system, according to an embodiment of the disclosure.

Embodiments of the disclosure provide systems and methods for examining a route traveled by a vehicle. The systems and methods may examine a route to determine the integrity of the route. For example, the systems and methods may examine a route to determine whether a portion of the route is damaged. The systems and methods may generate and transmit a coded signal into and through at least a portion of the route. The coded signal is received by a receiver, for example. The received coded signal is analyzed to determine the integrity of the route. The coded signal may be selected so as not to interfere with other route and/or vehicle systems, for example.

Embodiments of the disclosure provide systems and methods that may generate and transmit coded test signals with respect to a route, such as rails of a railroad, to test rail conductivity. The coded test signals may include non-repetitive sequence test signals that are not susceptible (or unlikely) to interfere with other systems connected to the route, such as rails. The systems and method may include forming a coded test signal, such as one or more coded pulses. Frequencies within each coded test signal may not be constant, and the sequence of coded pulses may be a random or pseudo random allocation in the time domain, such as a spreading code. The random signals may prevent or otherwise reduce the possibility of the coded test signals from creating one or more sustained frequency components on the rail(s) that may interfere with the correct or safe functioning of other systems. Moreover, the spreading code may be used to determine that the coded test signal transmitted through the route is confirmed as the intended coded test signal.

The coded test signal may include pulse groups of constant carrier frequency, or pulse groups that are frequency or phase modulated to a particular scheme. For example, if the coded test signals are at a primary frequency of 10 kHz and are keyed on and off at 1 kHz, an envelope of a test waveform may have a 1 kHz component on the route, which may interfere, or mix to create other frequency components on the route. In an embodiment, the 10 kHz signal may be keyed on and off at a constantly changing code. Accordingly, no steady state envelope frequency may be generated long enough to create interference.

Embodiments of the disclosure may be used with systems and methods disclosed in United States Patent Application Publication No. 2014/0138493, entitled "Route Examining System and Method," which is hereby incorporated by reference in its entirety.

The term "vehicle" as used herein can be defined as a mobile machine that transports at least one of a person, people, or a cargo. For instance, a vehicle can be, but is not limited to being, a rail car, an intermodal container, a locomotive, a marine vessel, mining equipment, construction equipment, an automobile, and the like. A "vehicle system" includes two or more vehicles that are interconnected with each other to travel along a route. For example, a vehicle system can include two or more vehicles that are directly connected to each other (for example, by a coupler) or that are indirectly connected with each other (for example, by one or more other vehicles and couplers). A vehicle system can be referred to as a consist, such as a rail vehicle consist.

"Software" or "computer program" as used herein includes, but is not limited to, one or more computer readable and/or executable instructions that cause a computer or other electronic device to perform functions, actions, and/or behave in a desired manner. The instructions may be embodied in various forms such as routines, algorithms, modules or programs including separate applications or code from dynamically linked libraries. Software may also be implemented in various forms such as a stand-alone program, a function call, a servlet, an applet, an application, instructions stored in a memory, part of an operating system or other type of executable instructions. "Computer" or "processing element" or "computer device" as used herein includes, but is not limited to, any programmed or programmable electronic device that can store, retrieve, and process data. "Non-transitory computer-readable media" include, but are not limited to, a CD-ROM, a removable flash memory card, a hard disk drive, a magnetic tape, and a floppy disk. "Memory", as used herein, refers to a storage device configured to store digital data or information which can be retrieved by a computer or processing element. "Controller," "unit," and/or "module," as used herein, can to the logic circuitry and/or processing elements and associated software or program involved in controlling a system. The terms "signal", "data", and "information" may be used interchangeably herein and may refer to digital or analog forms.

FIG. 1A illustrates a schematic diagram of a route examining system 10, according to an embodiment of the disclosure. The route examining system 10 may include a test signal transmission system 12 and a coded test signal receiving system 14. The coded test signal transmission system 12 operates to transmit or inject a coded test signal 16 into, through, and/or over a route 18 to the coded test signal receiving system 14. The transmitted coded test signal 16 may be received and analyzed by the coded test signal receiving system 14 to determine aspects of the route 18, such as the integrity of the route 18. For example, the coded test signal receiving system 14 may analyze the received coded test signal 16 to determine whether the route 18, or at least a portion thereof, is damaged.

The coded test signal transmission system 12 may be positioned on a vehicle within a vehicle system, for example. Similarly, the coded test signal receiving system 14 may be positioned on another vehicle within the vehicle system. Optionally, both the coded test signal transmission system 12 and the coded test signal receiving system 14 may be positioned on the same vehicle, such as a same vehicle within a vehicle system. Optionally, the coded test signal transmission system 12 may be positioned at a fixed wayside device along the route 18, while the coded test signal receiving system 14 may be positioned on a vehicle. Alternatively, the coded test signal transmission system 12 may be positioned on a vehicle, while the coded test signal transmission system 14 may be positioned at a fixed wayside device along the route 18. Also, alternatively, the coded test signal transmission system 12 may be positioned at a first fixed wayside device along the route 18, while the coded test signal receiving system 14 maybe positioned at a second fixed wayside device along the route 18.

The route 18 may be a body, surface, or medium on which a vehicle or vehicle system travels. In an embodiment, the route 18 may include or represent a body that is capable of conveying a signal between vehicles in a vehicle system, such as a conductive body capable of conveying an electrical signal (for example, a direct current, alternating current, radio frequency, or other signal).

In an embodiment, the coded test signal 16 may be or include a chirp signal. The coded test signal transmission system 12 may include a control unit 20 that is configured to transmit the coded test signal 16 to the coded test signal receiving system 14 over the route 18. The coded test signal 16 may be stored in a memory 22 of the coded test signal transmission system 12.

The coded test signal receiving system 14 may include a control unit 24 that is configured to receive the coded test signal 16 over the route 18. The control unit 24 may compare the received coded test signal 16 with code data stored in a memory 26. The code data stored in the memory allows the coded test signal receiving system 14 to determine whether the received coded test signal 16 has degraded, changed, or the like during transmission over the route 18. For example, the coded test signal receiving system 14 may be programmed to recognize that the received coded test signal 16 is to have certain aspects, such as one or more frequencies. If, however, one or more of those aspects do not match the coded data stored in the memory 26, the coded test signal receiving system 14 may determine that the route 18 is damaged, for example.

As noted, the coded test signal 16 transmitted by the coded test signal transmission system 12 may be or include a chirp signal. For example, the chirp signal may sweep from an initial frequency to an end frequency over a short period of time. The frequency range of the chirp signal may be chosen to be different than frequencies used by other systems along the route 18, in order to avoid interference therewith.

In one embodiment, the initial frequency may be 4.9 kHz and the end frequency may be 5.1 kHz. The chirp signal may sweep from the initial 4.9 kHz frequency to the end 5.1 kHz signal over a 20 millisecond (ms) time period. The memory 26 of the coded test signal receiving system 14 stores data regarding such a frequency sweep identification over the time period as coded data. As such, if the received coded test signal 16 varies from the chirp signal stored as coded data (such as if the received coded test signal 16 varies from the initial 4.9 kHz frequency and/or the 5.1 kHz end frequency), the coded test signal receiving system 14 may determine that the route 18 (or at least the portion disposed between the coded test signal transmission system 12 and the coded test signal receiving system 14) is damaged.

Alternatively, the chirp signal may be various other types of chirp signals. For example, the initial frequency may be greater or less than 4.9 kHz, the end frequency may be greater or less than 5.1 kHz, and the time period may be greater or less than 20 ms.

In an embodiment, the coded test signal 16 may be or include a chirp signal that changes or hops over a frequency spectrum. For example, instead of a frequency sweep from an initial frequency to an end frequency, the coded test signal 16 may be transmitted at a first frequency at a first time within a time duration, a second frequency at a second time within the time duration, and a third frequency at a third time within the time duration. The first frequency may be greater or less than the second frequency, which may be greater or less than the third frequency. The time duration may be 20 ms. For example, the first frequency may be 5.1 kHz, the second frequency may be 4.4 kHz, and the third frequency may be 5.7 kHz. Optionally, the frequencies may be greater or less than such examples. Further, more or less frequencies may be used over the time duration, and the time duration may be greater or less than 20 ms. For example, six different frequencies over a 10 ms time duration may be generated.

The coded test signal receiving system 14 stores the frequency hop pattern in the memory 26. As such, if the received coded test signal 16 includes different frequencies than those stored in the memory 26, the coded test signal receiving system 14 may determine that the route 18 is damaged. Further, the frequencies used in the coded test signal 16 may be different than those used by other systems along the route, in order to avoid interference therewith.

By hopping around different frequencies, not all the frequencies of the coded test signal 16 are in a frequency range of noise or interference. Accordingly, the coded test signal receiving system 14 may receive one or more frequencies of the coded test signal 16 and determine that the route 18 is sound. For example, if the coded test signal 16 includes five different frequencies over a time duration, the coded test signal receiving system 14 may determine that the route 18 is sound if the received coded test signal 16 includes one or more of the five frequencies. If, however, the coded test signal receiving system 14 does not receive the coded test signal 16 including at least one of the different frequencies, then the coded test signal receiving system 14 may determine that the route 18 is damaged. Alternatively, the coded test signal receiving system 14 may determine that the route 18 is damaged if the received coded test signal does not include at least two of the frequencies, for example.

Additionally, the coded test signal receiving system 14 may be unable to detect a signal at a particular frequency. The coded test signal receiving system 14 may then store the undetectable frequency in the memory 26, and communicate with the coded test signal transmission system 12 indicating that such frequency is unable to be received. Accordingly, the undetectable frequency may be indicative of noise or interference. As such, the coded test signal transmission system 12 may avoid transmitting the coded test signal 16 at the undetectable frequency.

One or both of the coded test signal transmission system 12 and the coded test signal receiving system 14 may receive reports from other systems along the route regarding the frequencies used by the other systems. Information regarding the frequencies used by the other systems may be stored in the memory 22 and/or the memory 26. The coded test signal transmission system 12 may therefore avoid transmitting at such frequencies, and the coded test signal receiving system 14 may avoid listening for the coded test signal 16 at such frequencies.

The frequencies of the coded test signal 16 may include one or more frequencies that are utilized by other systems along the route 18. However, the time duration of the transmitted coded test signal 16 may be short enough to not interfere with the other systems. For example, the coded test signal 16 may be 20 ms or less, which may be a short enough time to not interfere with the other systems. Further, the coded test signal transmission system 12 may transmit the coded test signal 16 at times when systems that utilize one or more similar frequencies are not transmitting at such frequencies. The memory 22 may store times when other systems are to transmit so that the coded test signal transmission system 12 avoids transmitting at those times.

In an embodiment, the coded test signal 16 may be or include a spread spectrum chirping coded signal, for example. The coded test signal transmission system 12 may generate a random or pseudo-random coded test signal. The coded test signal transmission system 12 may generate the coded test signal 16 and may switch the random or pseudo-random code on and off. The coded test signal 16 may change with every packet or burst that is transmitted by the coded test signal transmission system 12.

For example, the coded test signal 16 may include a ten bit random number encoded thereon. Alternatively, the coded test signal 16 may include a random number that is greater or less than 10 bits. The coded test signal 16 may be switched on and off with respect to the random number. The random number may change with each transmitted burst. The coded test signal receiving system 14 stores the random number for each burst within the memory 26. The coded test signal receiving system 14 may receive the random number sequences and compare it with coded data stored in the memory 26. A certain amount of noise within the route 18 may cause the coded test signal receiving system 14 to receive the coded test signal 16 as less than a full match of the random ten bit number. The coded test signal receiving system 14 may determine that the route 18 is damaged if a matching threshold has not been met. For example, the matching threshold may be no match of any of the random number of a burst sequence. Alternatively, the matching threshold may be less than a certain percentage of the random number, such as less than 25% of the random number.

The random or pseudo-random codes may be changed over time. As noted, the coded test signal transmission system 12 may be programmed to change the random codes at regular intervals, while the coded test signal receiving system 14 stores the changes as coded data within the memory 26.

The route examining system 10 may be used to examine the route 18 by transmitting the coded test signal 16 over the route 18 to the coded test signal receiving system 14. If the coded test signal 16 received by the coded test signal receiving system 14 matches coded data within the memory 26 of the coded test signal receiving system 14, the integrity of the route 18 may be confirmed. If, however, the received coded test signal 16 varies from the coded data stored within the coded test signal receiving system 14 by a predetermined amount (such as by being below a stored matching threshold), the route 18 may be determined to be damaged.

The coded test signal 16 may be used to compensate for noise generated within the route 18. For example, the coded test signal 16 may be or include a chirp signal that sweeps from an initial frequency to an end frequency and/or hops or changes among different frequencies. While noise may interfere with at least one of the frequencies within the chirp signal, the noise may not interfere with all of the frequencies. In an embodiment, the coded test signal 16 may be or include a spread spectrum chirping code, which may include one or more random or pseudo-random codes.

The frequencies, chirp range, chirping code, and/or the like for the coded test signal 16 may be selected so as to reduce interference with other systems along the route 18, such as wayside signaling systems. The unique characteristics of the coded test signal 16 may reduce the likelihood of receiving a false signal that may be generated from another source. The coded test signal receiving system 14 stores coded data that matches one or more aspects of the transmitted coded test signal 16, thereby ensuring that the coded test signal receiving system 14 receives the unique transmitted coded test signal 16. If one or more aspects of the received coded test signal 16 do not match the stored coded data, the coded test signal receiving system 14 may determine that the route 18, or at least a portion of the route 18 between the coded test signal transmission system 12 and the coded test signal receiving system 14, is damaged.

In one embodiment, the system 10 may be used with respect to a beacon signal. For example, the coded test signal transmission test unit 12 may send the coded test signal 16 to the coded test signal receiving system 14, which may be located on a remote vehicle, device, equipment, system, or the like. The route 18 may be other than a track on which the units 12 and 14 are positioned. For example, the route 18 may be an unconnected path between the units 12 and 14, such as a linear path through air or water. As an example, the coded test signal transmission system 12 may be in a black box of a vehicle that has crashed or is stranded. The coded test signal 16 transmitted by the coded test signal transmission system 12 may be a beacon signal that is transmitted to the coded test signal receiving system 14. The coded test signal receiving system 14 scans or listens for the coded test signal 16 in order to determine a location of the coded test signal transmission system.

Figure 1B:
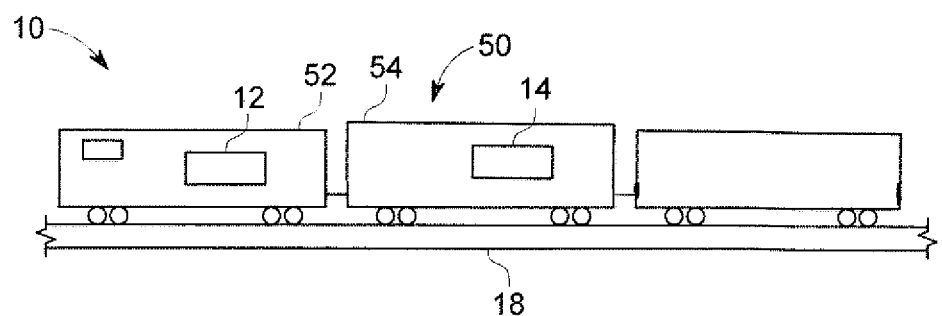
FIG. 1B illustrates a simplified diagram of a route examining system within a vehicle system on a route, according to an embodiment of the disclosure.

FIG. 1B illustrates a simplified diagram of the route examining system 10 within a vehicle system 50 on the route 18, according to an embodiment of the disclosure. As shown, the coded test signal transmission system 12 may be in or on a first vehicle 52 of the vehicle system 50, while the coded test signal receiving system 14 may be in or on a second vehicle 54 of the vehicle system 50. While not shown, each vehicle within the vehicle system 50 may have a coded test signal transmission system 12 and a coded test signal receiving system 14.

Figure 1C:
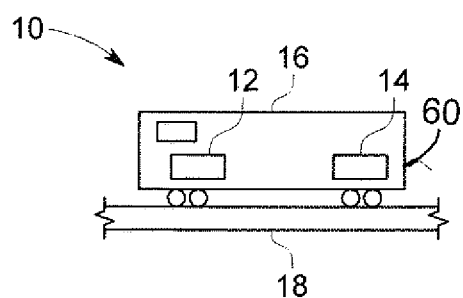
FIG. 1C illustrates a simplified diagram of a route examining system within a vehicle on a route, according to an embodiment of the disclosure.

FIG. 1C illustrates a simplified diagram of the route examining system 10 within a vehicle 60 on the route 18, according to an embodiment of the disclosure. As shown, both the coded test signal transmission system 12 and the coded test signal receiving system 14 may be on or in the same vehicle 60.

Figure 1D:
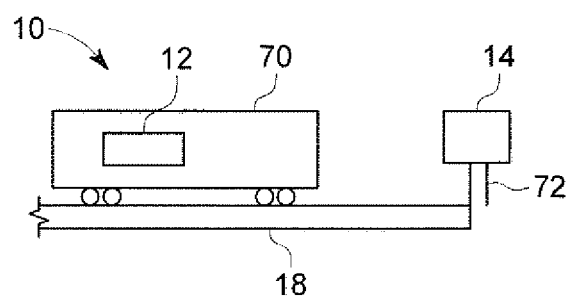
FIG. 1D illustrates a simplified diagram of a route examining system distributed between a vehicle and a wayside device on a route, according to an embodiment of the disclosure.

FIG. 1D illustrates a simplified diagram of the route examining system 10 distributed between a vehicle 70 and a wayside device 72 on the route 18, according to an embodiment of the disclosure. As shown, the vehicle 70 may include the coded test signal transmission system 12, while the wayside device 72 may include the coded test signal receiving system 14, or vice versa.

Figure 1E:
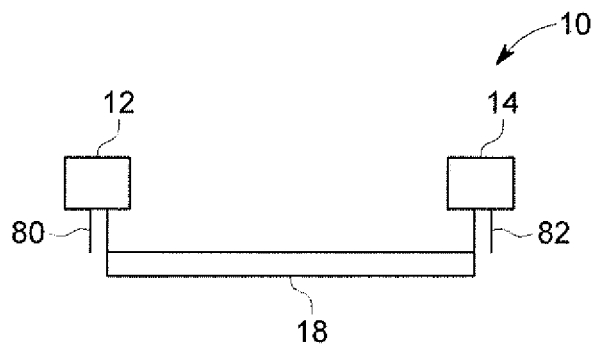
FIG. 1E illustrates a simplified diagram of a route examining system distributed between wayside devices on a route, according to an embodiment of the disclosure.

FIG. 1E illustrates a simplified diagram of the route examining system 10 distributed between wayside devices 80 and 82 on the route 18, according to an embodiment of the disclosure. The wayside device 80 may include the coded test signal transmission system 12, while the wayside device 82 may include the coded test signal receiving system 14, or vice versa.

Figure 2:
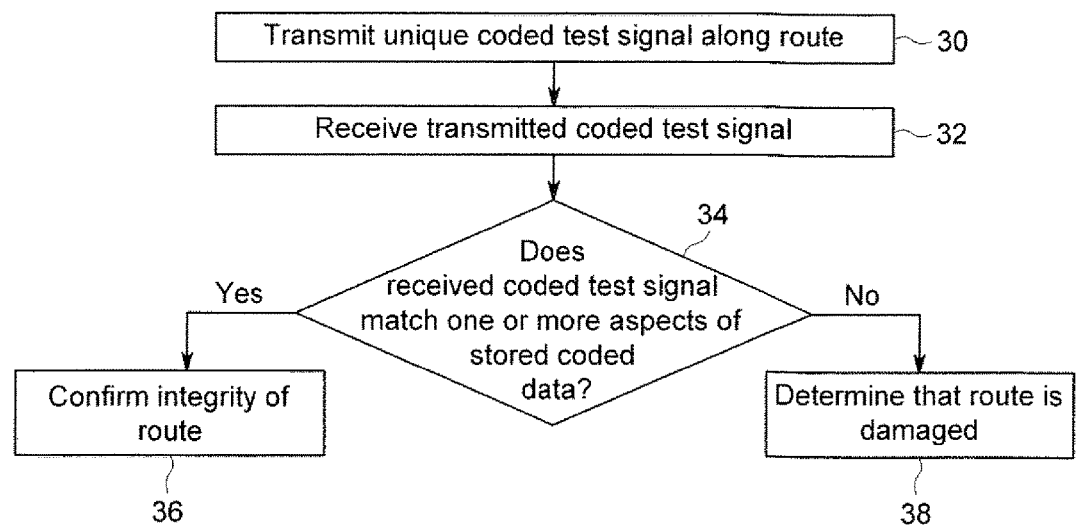
FIG. 2 illustrates a flow chart of a route examining method, according to an embodiment of the disclosure.

FIG. 2 illustrates a flow chart of a route examining method, according to an embodiment of the disclosure. At 30, a unique coded test signal is transmitted along a route. The transmitted coded test signal is received at 32. At 34, it is determined if the received coded test signal matches one or more aspects of stored coded data. The aspects may include an initial frequency, an end frequency, one or more other frequencies, one or more bits of a random or pseudo-random number sequence, and/or the like. If the received coded test signal matches one or more aspects of the stored coded data, the integrity of the route is confirmed at 36. If, however, the received coded test signal does not match one or more aspects of the stored coded data, the route is determined to be damaged at 38.

In an embodiment, the integrity of the route is confirmed in response to the received coded test signal matching all of the aspects of the stored coded data. In another embodiment, the integrity of the route is confirmed in response to the received coded test signal matching a threshold level (for example, a matching threshold) of aspects of the stored coded data. The threshold level may be a predetermined percentage of aspects, such as at least 50%. However, the threshold level may be greater or less than 50%, but more than 0. For example, the threshold level may be a certain percentage of transmitted frequencies. In another embodiment, the threshold level may be a certain portion of a random number sequence transmitted within the coded test signal.

Figure 3:
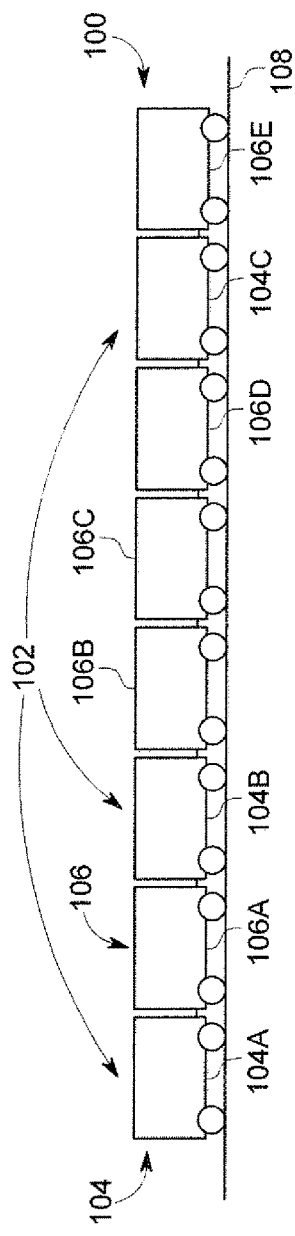
FIG. 3 illustrates a schematic diagram of a vehicle system having a route examining system, according to an embodiment of the disclosure.

FIG. 3 illustrates a schematic diagram of a vehicle system 100 having a route examining system 102, according to an embodiment of the disclosure. The route examining system 102 may be an example of the route examining system 10, shown and described with respect to FIG. 1A. As shown, the route examining system 102 is positioned on or within the vehicle system 100. Alternatively, the route examining system 102 may be positioned within a single vehicle of the vehicle system 100, between the vehicle system 100 and a wayside device, and/or between multiple wayside devices.

The vehicle system 100 may include several vehicles 104, 106 that are mechanically connected with each other to travel along a route 108. The vehicles 104 (for example, the vehicles 104A-C) represent propulsion-generating vehicles, such as vehicles that generate tractive effort or power in order to propel the vehicle system 100 along the route 108. In an embodiment, the vehicles 104 may represent rail vehicles such as locomotives. The vehicles 106 (for example, the vehicles 106A-E) represent non-propulsion generating vehicles, such as vehicles that do not generate tractive effort or power. In an embodiment, the vehicles 106 may represent rail cars. Alternatively, the vehicles 104, 106 may represent other types of vehicles. In another embodiment, one or more of the individual vehicles 104 and/or 106 represent a group of vehicles, such as a consist of locomotives or other vehicles.

The route examining system 102 may be distributed between or among two or more vehicles 104, 106 of the vehicle system 100. For example, the route examining system 102 may include two or more components that operate to identify potentially damaged sections of the route 108, with at least one component disposed on each of two different vehicles 104, 106 in the same vehicle system 100. In the illustrated embodiment, the examining system 102 is distributed between or among two different vehicles 104. Alternatively, the examining system 102 may be distributed among three or more vehicles 104, 106. Additionally or alternatively, the examining system 102 may be distributed between one or more vehicles 104 and one or more vehicles 106, and is not limited to being disposed onboard a single type of vehicle 104 or 106. As described below, in another embodiment, the examining system 102 may be distributed between a vehicle in the vehicle system and an off-board monitoring location, such as a wayside device.

In operation, the vehicle system 100 travels along the route 108. A first vehicle 104 electrically injects a coded test signal into the route 108. For example, the first vehicle 104A may apply a direct current, alternating current, radio frequency signal, or the like, to the route 108 as a coded test or examination signal. The coded test signal propagates through or along the route 108. A second vehicle 104B or 104C may monitor one or more characteristics of the route 108 when the coded test signal is injected into the route 108. Intermediate vehicles may receive and transmit the coded test signal between the first vehicle 104A and the second vehicle 104B or 104C.

The route examining system 102 may be distributed among two separate vehicles 104 and/or 106. In the illustrated embodiment, the route examining system 102 has components disposed onboard at least two of the propulsion-generating vehicles 104A, 104B, 104C. Additionally or alternatively, the route examining system 102 may include components disposed onboard at least one of the non-propulsion generating vehicles 106. For example, the route examining system 102 may be located onboard two or more propulsion-generating vehicles 104, two or more non-propulsion generating vehicles 106, or at least one propulsion-generating vehicle 104 and at least one non-propulsion generating vehicle 106.

In operation, during travel of the vehicle system 100 along the route 108, the route examining system 102 electrically injects a coded test or examination signal into the route 108 at a first vehicle 104 or 106 (for example, beneath the footprint of the first vehicle 104 or 106). For example, an onboard or off-board power source may be controlled to apply a direct current, alternating current, RF signal, or the like, to a track of the route 108. The route examining system 102 monitors characteristics of the route 108 at a second vehicle 104 or 106 of the same vehicle system 100 (for example, beneath the footprint of the second vehicle 104 or 106) in order to determine if the examination signal is detected in the route 108. For example, the voltage, current, resistance, impedance, or other electrical characteristic of the route 108 may be monitored at the second vehicle 104, 106 in order to determine if the coded test or examination signal is detected and/or if the examination signal has been altered. If the portion of the route 108 between the first and second vehicles conducts the coded test or examination signal to the second vehicle, then the coded test or examination signal may be detected by the route examining system 102. The route examining system 102 may determine that the route 108 (for example, the portion of the route 108 through which the examination signal propagated) is intact and/or not damaged.

On the other hand, if the portion of the route 108 between the first and second vehicles does not conduct the examination signal to the second vehicle (for example, such that the coded test or examination signal is not detected in the route 108 at the second vehicle), then the coded test or examination signal may not be detected by the route examining system 102. The route examining system 102 may determine that the route 108 (for example, the portion of the route 108 disposed between the first and second vehicles during the time period that the coded test or examination signal is expected or calculated to propagate through the route 108) is not intact and/or is damaged. For example, the route examining system 102 may determine that the portion of a track between the first and second vehicles is broken such that a continuous conductive pathway for propagation of the coded test or examination signal does not exist. The route examining system 102 can identify this section of the route as being a potentially damaged section of the route 108. In routes 108 that are segmented (for example, such as rail tracks that may have gaps), the route examining system 102 may transmit and attempt to detect multiple coded test or examination signals in order to prevent false detection of a broken portion of the route 108.

Because the coded test or examination signal may propagate relatively quickly through the route 108 (for example, faster than a speed at which the vehicle system 100 moves), the route 108 can be examined using the coded test or examination signal when the vehicle system 100 is moving, such as transporting cargo or otherwise operating at or above a non-zero, minimum speed limit of the route 108.

Additionally or alternatively, the route examining system 102 may detect one or more changes in the coded test or examination signal at the second vehicle. The coded test or examination signal may propagate through the route 108 from the first vehicle to the second vehicle. But, due to damaged portions of the route 108 between the first and second vehicles, one or more signal characteristics or aspects of the coded test or examination signal may have changed. For example, the signal-to-noise ratio, frequency, intensity, power, or the like, of the examination signal may be known or designated when injected into the route 108 at the first vehicle. One or more of these signal characteristics may change (for example, deteriorate or decrease) during propagation through a mechanically damaged or deteriorated portion of the route 108, even though the coded test or examination signal is received (for example, detected) at the second vehicle. The signal aspects or characteristics can be monitored upon receipt of the coded test or examination signal at the second vehicle. Based on changes in one or more of the signal aspects or characteristics, the route examining system 102 may identify the portion of the route 108 that is disposed between the first and second vehicles as being a potentially damaged portion of the route 108. For example, if the signal-to-noise ratio, frequency, intensity, power, or the like, of the coded test or examination signal decreases below a designated threshold and/or decreases by more than a designated threshold decrease, then the route examining system 102 may identify the section of the route 108 as being potentially damaged.

In response to identifying a section of the route 108 as being damaged or damaged, the route examining system 102 may initiate one or more responsive actions. For example, the route examining system 102 can automatically slow down or stop movement of the vehicle system 100. The route examining system 102 can automatically issue a warning signal to one or more other vehicle systems traveling nearby of the damaged section of the route 108 and where the damaged section of the route 108 is located. The route examining system 102 may automatically communicate a warning signal to a stationary wayside device located at or near the route 108 that notifies the device of the potentially damaged section of the route 108 and the location of the potentially damaged section. The stationary wayside device can then communicate a signal to one or more other vehicle systems traveling nearby of the potentially damaged section of the route 108 and where the potentially damaged section of the route 108 is located. The route examining system 102 may automatically issue an inspection signal to an off-board facility, such as a repair facility, that notifies the facility of the potentially damaged section of the route 108 and the location of the section. The facility may then send one or more inspectors to check and/or repair the route 108 at the potentially damaged section. Alternatively, the route examining system 102 may notify an operator of the potentially damaged section of the route 108 and the operator may then manually initiate one or more responsive actions.

Figure 4:
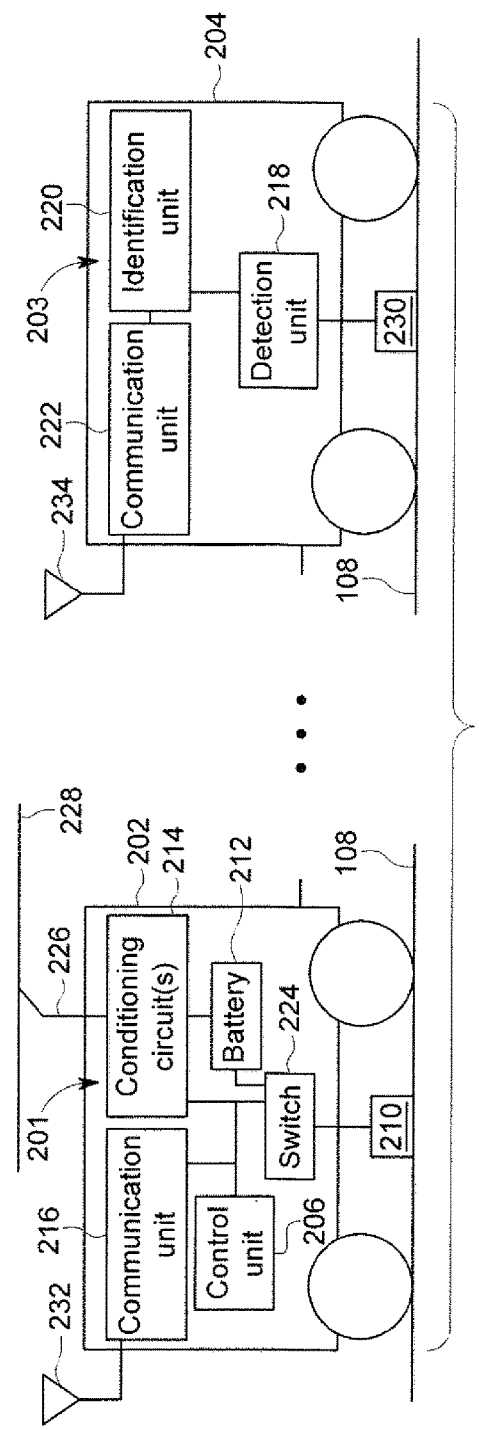
FIG. 4 illustrates a schematic diagram of a route examining system, according to an embodiment of the disclosure.

FIG. 4 illustrates a schematic diagram of a route examining system 200, according to an embodiment of the disclosure. The route examining system 200 may be an example of the route examining systems described with respect to FIGS. 1A-E and 3, for example. The route examining system 200 may be distributed between a first vehicle 202 and a second vehicle 204 in the same vehicle system. The vehicles 202, 204 may represent vehicles 104 and/or 106 of the vehicle system 100 shown in FIG. 3. In an embodiment, the vehicles 202, 204 represent two of the vehicles 104, such as the vehicle 104A and the vehicle 104B, the vehicle 104B and the vehicle 104C, or the vehicle 104A and the vehicle 104C. Alternatively, one or more of the vehicles 202, 204 may represent at least one of the vehicles 106. In another embodiment, the examining system 200 may be distributed among three or more of the vehicles 104 and/or 106.

The route examining system 200 may include several components described below that are disposed onboard the vehicles 202, 204. For example, the illustrated embodiment of the route examining system 200 includes a coded test signal transmission system 201, which may include a control unit 208, an application device 210, an onboard power source 212 ("Battery" in FIG. 4), one or more conditioning circuits 214, a communication unit 216, and one or more switches 224 disposed onboard the first vehicle 202. The examining system 200 may also include a coded test signal receiving system 203, which may include a detection unit 218, an identification unit 220, a detection device 230, and a communication unit 222 disposed onboard the second vehicle 204. Alternatively, one or more of the control unit 208, application device 210, power source 212, conditioning circuits 214, communication unit 216, and/or switch 224 may be disposed onboard the second vehicle 204 and/or another vehicle in the same vehicle system, and/or one or more of the detection unit 218, identification unit 220, detection device 230, and communication unit 222 may be disposed onboard the first vehicle 202 and/or another vehicle in the same vehicle system.

The control unit 206 controls supply of electric current to the application device 210. In an embodiment, the application device 210 includes one or more conductive bodies that engage the route 108 as the vehicle system that includes the vehicle 202 travels along the route 108. For example, the application device 210 can include a conductive shoe, brush, or other body that slides along an upper and/or side surface of a track such that a conductive pathway is created that extends through the application device 210 and the track. Additionally or alternatively, the application device 210 can include a conductive portion of a wheel of the first vehicle 202, such as the conductive outer periphery or circumference of the wheel that engages the route 108 as the first vehicle 202 travels along the route 108. In another embodiment, the application device 210 may be inductively coupled with the route 108 without engaging or touching the route 108 or any component that engages the route 108.

The application device 210 is conductively coupled with the switch 224, which can represent one or more devices that control the flow of electric current from the onboard power source 212 and/or the conditioning circuits 214. The switch 224 can be controlled by the control unit 206 so that the control unit 206 can turn on or off the flow of electric current through the application device 210 to the route 108. In an embodiment, the switch 224 also can be controlled by the control unit 206 to vary one or more waveforms and/or waveform characteristics (for example, phase, frequency, amplitude, and the like) of the current that is applied to the route 108 by the application device 210.

The onboard power source 212 represents one or more devices capable of storing electric energy, such as one or more batteries, capacitors, flywheels, and the like. Additionally or alternatively, the power source 212 may represent one or more devices capable of generating electric current, such as an alternator, generator, photovoltaic device, gas turbine, or the like. The power source 212 is coupled with the switch 224 so that the control unit 206 can control when the electric energy stored in the power source 212 and/or the electric current generated by the power source 212 is conveyed as electric current (for example, direct current, alternating current, an RF signal, or the like) to the route 108 via the application device 210.

The conditioning circuit 214 represents one or more circuits and electric components that change characteristics of electric current. For example, the conditioning circuit 214 may include one or more inverters, converters, transformers, batteries, capacitors, resistors, inductors, and the like. In the illustrated embodiment, the conditioning circuit 214 is coupled with a connecting assembly 226 that is configured to receive electric current from an off-board source. For example, the connecting assembly 226 may include a pantograph that engages an electrified conductive pathway 228 (for example, a catenary) extending along the route 108 such that the electric current from the catenary 228 is conveyed via the connecting assembly 226 to the conditioning circuit 214. Additionally or alternatively, the electrified conductive pathway 228 may represent an electrified portion of the route 108 (for example, an electrified rail) and the connecting assembly 226 may include a conductive shoe, brush, portion of a wheel, or other body that engages the electrified portion of the route 108. Electric current is conveyed from the electrified portion of the route 108 through the connecting assembly 226 and to the conditioning circuit 214.

The electric current that is conveyed to the conditioning circuit 214 from the power source 212 and/or the off-board source (for example, via the connecting assembly 226) can be altered by the conditioning circuit 214. For example, the conditioning circuit 214 can change the voltage, current, frequency, phase, magnitude, intensity, waveform, and the like, of the current that is received from the power source 212 and/or the connecting assembly 226. The modified current can be the coded test or examination signal that is electrically injected into the route 108 by the application device 210. Additionally or alternatively, the control unit 206 can form the coded test or examination signal by controlling the switch 224. For example, the examination signal can be formed by turning the switch 224 on to allow current to flow from the conditioning circuit 214 and/or the power source 212 to the application device 210.

In an embodiment, the control unit 206 may control the conditioning circuit 214 to form the coded test or examination signal. For example, the control unit 206 may control the conditioning circuit 214 to change the voltage, current, frequency, phase, magnitude, intensity, waveform, and the like, of the current that is received from the power source 212 and/or the connecting assembly 226 to form the coded test or examination signal.

The coded test or examination signal may be conducted through the application device 210 to the route 108, and is electrically injected into a conductive portion of the route 108. For example, the coded test or examination signal may be conducted into a conductive track of the route 108. In another embodiment, the application device 210 may not directly engage (for example, touch) the route 108, but may be wirelessly coupled with the route 108 in order to electrically inject the coded test or examination signal into the route 108 (for example, via induction).

The conductive portion of the route 108 that extends between the first and second vehicles 202, 204 during travel of the vehicle system may form a track circuit through which the coded test or examination signal may be conducted. The first vehicle 202 can be coupled (for example, coupled physically, coupled wirelessly, among others) to the track circuit by the application device 210. The power source (for example, the onboard power source 212 and/or the off-board electrified conductive pathway 228) can transfer power (for example, the coded test or examination signal) through the track circuit toward the second vehicle 204.

By way of example and not limitation, the first vehicle 202 can be coupled to a track of the route 108, and the track can be the track circuit that extends and conductively couples one or more components of the route examining system 200 on the first vehicle 202 with one or more components of the examining system 200 on the second vehicle 204.

In an embodiment, the control unit 206 includes or represents a manager component. Such a manager component can be configured to activate a transmission of electric current into the route 108 via the application device 210. In another instance, the manager component can activate or deactivate a transfer of the portion of power from the onboard and/or off-board power source to the application device 210, such as by controlling the switch and/or conditioning circuit. Moreover, the manager component can adjust parameter(s) associated with the portion of power that is transferred to the route 108. For instance, the manager component can adjust an amount of power transferred, a frequency at which the power is transferred (for example, a pulsed power delivery, AC power, among others), a duration of time the portion of power is transferred, among others. Such parameter(s) can be adjusted by the manager component based on at least one of a geographic location of the vehicle or the device or an identification of the device (for example, type, location, make, model, among others).

The manager component can leverage a geographic location of the vehicle or the device in order to adjust a parameter for the portion of power that can be transferred to the device from the power source. For instance, the amount of power transferred can be adjusted by the manager component based on the device power input. By way of example and not limitation, the portion of power transferred can meet or be below the device power input in order to reduce risk of damage to the device. In another example, the geographic location of the vehicle and/or the device can be utilized to identify a particular device and, in turn, a power input for such device. The geographic location of the vehicle and/or the device can be ascertained by a location on a track circuit, identification of the track circuit, Global Positioning Service (GPS), among others.

The detection unit 218 disposed onboard the second vehicle 204 as shown in FIG. 4 monitors the route 108 to attempt to detect the coded test or examination signal that is injected into the route 108 by the first vehicle 202. The detection unit 218 is coupled with the detection device 230. In an embodiment, the detection device 230 includes one or more conductive bodies that engage the route 108 as the vehicle system that includes the vehicle 204 travels along the route 108. For example, the detection device 230 can include a conductive shoe, brush, or other body that slides along an upper and/or side surface of a track such that a conductive pathway is created that extends through the detection device 230 and the track. Additionally or alternatively, the detection device 230 can include a conductive portion of a wheel of the second vehicle 204, such as the conductive outer periphery or circumference of the wheel that engages the route 108 as the second vehicle 204 travels along the route 108. In another embodiment, the detection device 230 may be inductively coupled with the route 108 without engaging or touching the route 108 or any component that engages the route 108.

The detection unit 218 may monitor one or more characteristics of the route 108 using the detection device 230. For example, the voltage of a direct current conducted by the route 108 may be detected by monitoring the voltage conducted by from the route 108 to the detection device 230 and/or the current (for example, frequency, amps, phases, or the like) of an alternating current or RF signal being conducted by the route 108 may be detected by monitoring the current conducted by the route 108 to the detection device 230. As another example, the signal-to-noise ratio of a signal being conducted by the detection device 230 from the route 108 may be detected by the detection unit 218 examining the signal conducted by the detection device 230 (for example, a received signal) and comparing the received signal to a designated signal. For example, the examination signal that is injected into the route 108 using the application device 210 may include a designated signal or portion of a designated signal. The detection unit 218 may compare the received signal that is conducted from the route 108 into the detection device 230 with this designated signal in order to measure a signal-to-noise ratio of the received signal.

The detection unit 218 determines one or more characteristics of the signal (for example, voltage, frequency, phase, waveform, intensity, or the like) that is received (for example, picked up) by the detection device 230 from the route 108 and reports the characteristics of the received signal to the identification unit 220. If no signal is received by the detection device 230, then the detection unit 218 may report the absence of such a signal to the identification unit 220. For example, if the detection unit 218 does not detect at least a designated voltage, designated current, or the like, as being received by the detection device 230, then the detection unit 218 may not detect any received signal. Alternatively or additionally, the detection unit 218 may communicate the detection of a signal that is received by the detection device 230 only upon detection of the signal by the detection device 230.

In an embodiment, the detection unit 218 may determine the characteristics of the signals received by the detection device 230 in response to a notification received from the control unit 206 in the first vehicle 202. For example, when the control unit 206 is to cause the application device 210 to inject the examination signal into the route 108, the control unit 206 may direct the communication unit 216 to transmit a notification signal to the detection device 230 via the communication unit 222 of the second vehicle 204. The communication units 216, 222 may include respective antennas 232, 234 and associated circuitry for wirelessly communicating signals between the vehicles 202, 204, and/or with off-board locations. The communication unit 216 may wirelessly transmit a notification to the detection unit 218 that instructs the detection unit 218 as to when the examination signal is to be input into the route 108. Additionally or alternatively, the communication units 216, 222 may be connected via one or more wires, cables, and the like, such as a multiple unit (MU) cable, train line, or other conductive pathway(s), to allow communication between the communication units 216, 222.

The detection unit 218 may begin monitoring signals received by the detection device 230. For example, the detection unit 218 may not begin or resume monitoring the received signals of the detection device 230 unless or until the detection unit 218 is instructed that the control unit 206 is causing the injection of the examination signal into the route 108. Alternatively or additionally, the detection unit 218 may periodically monitor the detection device 230 for received signals and/or may monitor the detection device 230 for received signals upon being manually prompted by an operator of the examining system 200.

The identification unit 220 receives the characteristics of the received signal from the detection unit 218 and determines if the characteristics indicate receipt of all or a portion of the examination signal injected into the route 108 by the first vehicle 202. Although the detection unit 218 and the identification unit 220 are shown as separate units, the detection unit 218 and the identification unit 220 may refer to the same unit. For example, the detection unit 218 and the identification unit 220 may be a single hardware component disposed onboard the second vehicle 204.

The identification unit 220 examines the characteristics and determines if the characteristics indicate that the section of the route 108 disposed between the first vehicle 202 and the second vehicle 204 is damaged or at least partially damaged. For example, if the application device 210 injected the examination signal into a track of the route 108 and one or more characteristics (for example, voltage, current, frequency, intensity, signal-to-noise ratio, and the like) of the coded test or examination signal are not detected by the detection unit 218, then, the identification unit 220 may determine that the section of the track that was disposed between the vehicles 202, 204 is broken or otherwise damaged such that the track cannot conduct the examination signal. Additionally or alternatively, the identification unit 220 can examine the signal-to-noise ratio of the signal detected by the detection unit 218 and determine if the section of the route 108 between the vehicles 202, 204 is potentially broken or damaged. For example, the identification unit 220 may identify this section of the route 108 as being broken or damaged if the signal-to-noise ratio of one or more (or at least a designated amount) of the received signals is less than a designated ratio.

The identification unit 220 may include or be communicatively coupled (for example, by one or more wired and/or wireless connections that allow communication) with a location determining unit that can determine the location of the vehicle 204 and/or vehicle system. For example, the location determining unit may include a GPS unit or other device that can determine where the first vehicle and/or second vehicle are located along the route 108. The distance between the first vehicle 202 and the second vehicle 204 along the length of the vehicle system may be known to the identification unit 220, such as by inputting the distance into the identification unit 220 using one or more input devices and/or via the communication unit 222.

The identification unit 220 can identify which section of the route 108 is potentially damaged based on the location of the first vehicle 202 and/or the second vehicle 204 during transmission of the examination signal through the route 108. For example, the identification unit 220 can identify the section of the route 108 that is within a designated distance of the vehicle system, the first vehicle 202, and/or the second vehicle 204 as the potentially damaged section when the identification unit 220 determines that the examination signal is not received or has a decreased signal-to-noise ratio.

Additionally or alternatively, the identification unit 220 can identify which section of the route 108 is potentially damaged based on the locations of the first vehicle 202 and the second vehicle 204 during transmission of the examination signal through the route 108, the direction of travel of the vehicle system that includes the vehicles 202, 204, the speed of the vehicle system, and/or a speed of propagation of the examination signal through the route 108. The speed of propagation of the examination signal may be a designated speed that is based on one or more of the material(s) from which the route 108 is formed, the type of examination signal that is injected into the route 108, and the like. In an embodiment, the identification unit 220 may be notified when the examination signal is injected into the route 108 via the notification provided by the control unit 206. The identification unit 220 can then determine which portion of the route 108 is disposed between the first vehicle 202 and the second vehicle 204 as the vehicle system moves along the route 108 during the time period that corresponds to when the examination signal is expected to be propagating through the route 108 between the vehicles 202, 204 as the vehicles 202, 204 move. This portion of the route 108 may be the section of potentially damaged route that is identified.

It is to be understood that the route examining systems shown and described with respect to FIGS. 3 and 4 are examples. Various other types of route examining systems that employ coded test or examination signals as described above with respect to FIGS. 1A-E and 2 may be employed.

In an embodiment, a system may include a coded test signal transmission system configured to transmit a unique coded test signal along a route, and a coded test signal receiving system configured to receive the unique coded test signal along the route. The unique coded test signal received by the coded test signal receiving system may be used to determine one or more characteristics of the route.

In one embodiment, the coded test signal transmission system is on or within a first vehicle, and the coded test signal receiving system is on or within a second vehicle that is separate and distinct from the first vehicle. In another embodiment, the coded test signal transmission system and the coded test signal receiving system are on the same vehicle. In yet another embodiment, one of the coded test signal transmission system or the coded test signal receiving system is on or within a vehicle, and the other of the coded test signal transmission system or the coded test signal receiving system is on or within a wayside device positioned on the route. Alternatively, one of the coded test signal transmission system or the coded test signal receiving system may be on or within a first wayside device positioned on the route, and the other of the coded test signal transmission system or the coded test signal receiving system may be on or within a second wayside device positioned on the route.

The coded test signal may include a chirp signal. The chirp signal may be transmitted over at least two frequencies during a period of time. The coded test signal receiving system may store coded data that is compared to the chirp signal received by the coded test signal receiving system.

The coded test signal receiving system may be configured to determine one or more undetectable frequencies. The coded test signal receiving system may be configured to communicate with the coded test signal transmission system to prevent the coded test signal transmission system from transmitting the coded test signal at the one or more undetectable frequencies.

One or both the coded test signal transmitting system and the coded test signal receiving system may be configured to determine one or more avoided frequencies that are used by other systems along the route. The coded test signal transmitting system may avoid transmitting the coded test signal using the one or more avoided frequencies.

In an embodiment, the coded test signal may include a spread spectrum chirping coded signal, which may include a random or pseudo-random signal. The coded test signal transmission system may be configured to switch the spread spectrum chirping coded signal between on and off states. The coded test signal transmission system may change the spread spectrum chirping coded signal each time the coded test signal transmission system switches the spread spectrum chirping coded signal to the on state.

The coded test signal receiving system may determine that the route is damaged in response to the coded test signal that is received by the coded test signal receiving system failing to meet a matching threshold.

An embodiment provides a method that may include receiving a unique coded test signal transmitted by a coded test signal transmission system along a route at a coded test signal receiving system, and using the unique coded test signal received by the coded test signal receiving system to determine one or more characteristics of the route.

The receiving operation may include receiving the coded test signal as a chirp signal that is transmitted over at least two frequencies during a period of time. The method may include storing coded data at the coded test signal receiving system, and comparing the chirp signal received by the coded test signal receiving system to the coded data.

The method may include determining one or more undetectable frequencies, and preventing transmission of the coded test signal transmission system at the one or more undetectable frequencies.

The method may include determining one or more avoided frequencies that are used by other systems along the route, and avoiding transmission of the coded test signal using the one or more avoided frequencies.

The method may include determining at least one of: one or more avoided frequencies that are used by other systems along the route; and/or one or more undetectable frequencies. The method further includes at least one of preventing or avoiding transmission of the unique coded test signal by the coded test signal transmission system at the at least one of the one or more avoided frequencies and/or the one or more undetectable frequencies.

In an embodiment, the receiving operation includes receiving the coded test signal as a spread spectrum chirping coded signal including a random signal. The method may include switching the spread spectrum chirping coded signal between on and off states, and changing the spread spectrum chirping coded signal each time the coded test signal transmission switches the spread spectrum chirping coded signal to the on state.

The using operation may include determining that the route is damaged in response to a received coded test signal failing to meet a matching threshold.

In another embodiment, a system (e.g., a route examining system) comprises a first sub-system (e.g., a receiving system, such as a coded test signal receiving system) configured to receive a unique coded test signal transmitted by a second sub-system (e.g., a transmission system, such as a coded test signal transmission system) along a route. The first sub-system is configured to determine one or more characteristics of the route based on the unique coded test signal as received by the first sub-system. Alternatively or additionally, the first sub-system is configured to communicate information about the unique coded test signal as received by the first sub-system to another sub-system that is not the first sub-system (e.g., the another system is the second sub-system or a third sub-system), for the another sub-system to determine the one or more characteristics of the route based on the information.

In another embodiment, a system (e.g., a route examining system) comprises a second system/sub-system (e.g., a transmission system, such as a coded test signal transmission system) configured to transmit a unique coded test signal along a route, and a first system/sub-system (e.g., a receiving system, such as a coded test signal receiving system) configured to receive the unique coded test signal along the route. At least one of the first system, the second system, or another, third system (e.g., another sub-system of the route examining system) is configured to determine one or more characteristics of the route based on the unique coded test signal as received by the first system. For example, the first system (e.g., receiving system) may be configured to determine the one or more characteristics of the route based on the unique coded test signal as received by the first system. As another example, the second system (e.g., transmission system) may be configured to determine the one or more characteristics of the route based on the unique coded test signal as received by the first system, e.g., the first system may be configured to gauge or ascertain one or more aspects or characteristics of the unique coded test signal as received by the first system, and to communicate information about the aspects or characteristics back to the second system. As another example, the third system (which may or may not be separate from the second system and/or the first system) may be configured to determine the one or more characteristics of the route based on the unique coded test signal as received by the first system, e.g., the first system may be configured to gauge or ascertain one or more aspects or characteristics of the unique coded test signal as received by the first system, and to communicate information about the aspects or characteristics to the third system.

In another embodiment, a system (e.g., a route examining system) comprises a second system/sub-system (e.g., a transmission system, such as a coded test signal transmission system) configured to transmit a unique coded test signal along a route, and a first system (e.g., a receiving system, such as a coded test signal receiving system) configured to receive the unique coded test signal along the route. At least one of the first system, the second system, or another, third system (e.g., another sub-system of the route examining system) is configured to determine one or more characteristics of the route based on the unique coded test signal as received by the first system. The second system is on or within a first vehicle, and the first system is on or within a second vehicle that is separate and distinct from the first vehicle.

In another embodiment, a system (e.g., a route examining system) comprises a second system/sub-system (e.g., a transmission system, such as a coded test signal transmission system) configured to transmit a unique coded test signal along a route, and a first system (e.g., a receiving system, such as a coded test signal receiving system) configured to receive the unique coded test signal along the route. At least one of the first system, the second system, or another, third system (e.g., another sub-system of the route examining system) is configured to determine one or more characteristics of the route based on the unique coded test signal as received by the first system. The second system is on board (e.g., on or within) a vehicle, and the first system is also on board the same vehicle.

In another embodiment, a system (e.g., a route examining system) comprises a second system/sub-system (e.g., a transmission system, such as a coded test signal transmission system) configured to transmit a unique coded test signal along a route, and a first system (e.g., a receiving system, such as a coded test signal receiving system) configured to receive the unique coded test signal along the route. At least one of the first system, the second system, or another, third system (e.g., another sub-system of the route examining system) is configured to determine one or more characteristics of the route based on the unique coded test signal as received by the first system. One of the first system or the second system is on or within a vehicle, and the other of the first system or the second system is on or within a wayside device positioned on the route.

In another embodiment, a system (e.g., a route examining system) comprises a second system/sub-system (e.g., a transmission system, such as a coded test signal transmission system) configured to transmit a unique coded test signal along a route, and a first system (e.g., a receiving system, such as a coded test signal receiving system) configured to receive the unique coded test signal along the route. At least one of the first system, the second system, or another, third system (e.g., another sub-system of the route examining system) is configured to determine one or more characteristics of the route based on the unique coded test signal as received by the first system. One of the first system or the second system is on or within a first wayside device positioned on the route, and the other of the first system or the second system is on or within a second wayside device positioned on the route.

In another embodiment, a system (e.g., a route examining system) comprises a second system/sub-system (e.g., a transmission system, such as a coded test signal transmission system) configured to transmit a unique coded test signal, comprising a chirp signal, along a route, and a first system (e.g., a receiving system, such as a coded test signal receiving system) configured to receive the unique coded test signal along the route. At least one of the first system, the second system, or another, third system (e.g., another sub-system of the route examining system) is configured to determine one or more characteristics of the route based on the unique coded test signal as received by the first system. The second system may be configured to transmit the chirp signal over at least two frequencies during a period of time. The first system may be configured to store coded data that is compared to the chirp signal received by the first system.

In another embodiment, a system (e.g., a route examining system) comprises a second system/sub-system (e.g., a transmission system, such as a coded test signal transmission system) configured to transmit a unique coded test signal along a route, and a first system (e.g., a receiving system, such as a coded test signal receiving system) configured to receive the unique coded test signal along the route. At least one of the first system, the second system, or another, third system (e.g., another sub-system of the route examining system) is configured to determine one or more characteristics of the route based on the unique coded test signal as received by the first system. The first system is configured to determine one or more undetectable frequencies, and to communicate with the second system to prevent the second system from transmitting the unique coded test signal at the one or more undetectable frequencies.

In another embodiment, a system (e.g., a route examining system) comprises a second system/sub-system (e.g., a transmission system, such as a coded test signal transmission system) configured to transmit a unique coded test signal along a route, and a first system (e.g., a receiving system, such as a coded test signal receiving system) configured to receive the unique coded test signal along the route. At least one of the first system, the second system, or another, third system (e.g., another sub-system of the route examining system) is configured to determine one or more characteristics of the route based on the unique coded test signal as received by the first system. One or both of the second system or the first system is configured to determine one or more avoided frequencies that are used by other systems along the route. The second system is configured to avoid transmitting the coded test signal using the one or more avoided frequencies.

In another embodiment, a system (e.g., a route examining system) comprises a second system/sub-system (e.g., a transmission system, such as a coded test signal transmission system) configured to transmit a unique coded test signal, comprising a spread spectrum chirping coded signal, along a route, and a first system (e.g., a receiving system, such as a coded test signal receiving system) configured to receive the unique coded test signal along the route. At least one of the first system, the second system, or another, third system (e.g., another sub-system of the route examining system) is configured to determine one or more characteristics of the route based on the unique coded test signal as received by the first system. The spread spectrum chirping coded signal may include a random signal. Additionally or alternatively, the second system may be configured to switch the spread spectrum chirping chirping coded signal between on and off states, and to change the spread spectrum chirping coded signal each time the second system switches the spread spectrum chirping coded signal to the on state.

In another embodiment, a system (e.g., a route examining system) comprises a second system/sub-system (e.g., a transmission system, such as a coded test signal transmission system) configured to transmit a unique coded test signal, comprising a spread spectrum chirping coded signal, along a route, and a first system (e.g., a receiving system, such as a coded test signal receiving system) configured to receive the unique coded test signal along the route. At least one of the first system, the second system, or another, third system (e.g., another sub-system of the route examining system) is configured to determine one or more characteristics of the route based on the unique coded test signal as received by the first system. The first system is configured to determine that the route is damaged in response to the unique coded test signal that is received by the first system failing to meet a matching threshold.

In another embodiment, a system (e.g., a route examining system) comprises a first sub-system, which comprises a coded test signal receiving system, and a second sub-system, which comprises a coded test signal transmission system. The coded test signal transmission system is configured to transmit a unique coded test signal along a route. The coded test signal receiving system is configured to receive the unique coded test signal along the route. The unique coded test signal received by the coded test signal receiving system is used to determine one or more characteristics of the route. For example, the coded test signal receiving system may be configured to determine the one or more characteristics of the route based on the unique coded test signal as received by the coded test signal receiving system. Alternatively or additionally, the coded test signal receiving system may be configured to communicate information about the unique coded test signal as received by the coded test signal receiving system to another sub-system that is not the coded test signal receiving system (e.g., the another system might be the coded test signal transmission system or a third sub-system), for the another sub-system to determine the one or more characteristics of the route based on the information.

In another embodiment, a system (e.g., a route examining system) comprises a first sub-system, which comprises a coded test signal receiving system, and a second sub-system, which comprises a coded test signal transmission system. The coded test signal transmission system is configured to transmit a unique coded test signal along a route. The coded test signal receiving system is configured to receive the unique coded test signal along the route. The unique coded test signal received by the coded test signal receiving system is used to determine one or more characteristics of the route. For example, the coded test signal receiving system may be configured to determine the one or more characteristics of the route based on the unique coded test signal as received by the coded test signal receiving system. Alternatively or additionally, the coded test signal receiving system may be configured to communicate information about the unique coded test signal as received by the coded test signal receiving system to another sub-system that is not the coded test signal receiving system (e.g., the another system might be the coded test signal transmission system or a third sub-system), for the another sub-system to determine the one or more characteristics of the route based on the information. One of the coded test signal transmission system or the coded test signal receiving system is on or within a first vehicle, and wherein the other of the coded test signal transmission system or the coded test signal receiving system is one of: on or within a second vehicle that is separate and distinct from the first vehicle; or on or within the same first vehicle; or on or within a wayside device positioned on the route.

The systems described above may include one or more control units, circuits, or the like, such as processing devices that may include one or more microprocessors, microcontrollers, integrated circuits, memory, such as read-only and/or random access memory, and the like. The systems may include any suitable computer-readable media used for data storage. For example, the systems may include computer-readable media. The computer-readable media are configured to store information that may be interpreted by the systems. The information may be data or may take the form of computer-executable instructions, such as software applications, that cause a microprocessor or other such control unit within the systems to perform certain functions and/or computer-implemented methods. The computer-readable media may include computer storage media and communication media. The computer storage media may include volatile and non-volatile media, removable and non-removable media implemented in any method or technology for storage of information such as computer-readable instructions, data structures, program modules or other data. The computer storage media may include, but are not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which may be used to store desired information and that may be accessed by components of the system.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein.

The above-described embodiments (and/or aspects thereof) may be used in combination with each other. In addition, many modifications may be made to adapt a particular situation or material to the teachings of the inventive subject matter without departing from its scope. While the dimensions and types of materials described herein are intended to define the parameters of the inventive subject matter, they are by no means limiting and are exemplary embodiments. Many other embodiments will be apparent to one of ordinary skill in the art upon reviewing the above description. The scope of the inventive subject matter should, therefore, be determined with reference to the appended clauses, along with the full scope of equivalents to which such clauses are entitled. In the appended clauses, the terms "including" and "in which" are used as the plain-English equivalents of the respective terms "comprising" and "wherein." Moreover, in the following clauses, the terms "first," "second," and "third," etc. are used merely as labels, and are not intended to impose numerical requirements on their objects. Further, the limitations of the following clauses are not written in means-plus-function format and are not intended to be interpreted based on 35 U.S.C. § 112(f), unless and until such clause limitations expressly use the phrase "means for" followed by a statement of function void of further structure.

This written description uses examples to disclose several embodiments of the inventive subject matter and also to enable a person of ordinary skill in the art to practice the embodiments of the inventive subject matter, including making and using any devices or systems and performing any incorporated methods. The patentable scope of the inventive subject matter is defined by the clauses, and may include other examples that occur to those of ordinary skill in the art. Such other examples are intended to be within the scope of the clauses if they have structural elements that do not differ from the literal language of the clauses, or if they include equivalent structural elements with insubstantial differences from the literal languages of the clauses.

The invention claimed is:

1. A system comprising:
a coded test signal transmission system configured to transmit a unique coded test signal along a route, wherein the unique coded test signal comprises a spread spectrum chirping coded signal, wherein the coded test signal transmission system is configured to switch the spread spectrum chirping coded signal between on and off states, and wherein the coded test signal transmission system is configured to change the spread spectrum chirping coded signal each time the coded test signal transmission system switches the spread spectrum chirping coded signal to the on state; and
a coded test signal receiving system configured to receive the unique coded test signal along the route,
wherein the unique coded test signal received by the coded test signal receiving system is used to determine one or more characteristics of the route,
wherein the coded test signal transmission system is configured to transmit the unique coded test signal over at least two frequencies during a period of time, and wherein the coded test signal receiving system is configured to store coded data that is compared to the unique coded test signal received by the coded test signal receiving system.

2. The system of claim 1, wherein the coded test signal transmission system is on or within a first vehicle, and wherein the coded test signal receiving system is on or within a second vehicle that is separate and distinct from the first vehicle.

3. The system of claim 1, wherein the coded test signal transmission system is on or within a vehicle, and the coded test signal receiving system is on or within the same vehicle.

4. The system of claim 1, wherein one of the coded test signal transmission system or the coded test signal receiving system is on or within a vehicle, and wherein the other of the coded test signal transmission system or the coded test signal receiving system is on or within a wayside device positioned on the route.

5. The system of claim 1, wherein one of the coded test signal transmission system or the coded test signal receiving system is on or within a first wayside device positioned on the route, and wherein the other of the coded test signal transmission system or the coded test signal receiving system is on or within a second wayside device positioned on the route.

6. The system of claim 1, wherein the coded test signal receiving system is configured to determine one or more undetectable frequencies, and wherein the coded test signal receiving system is configured to communicate with the coded test signal transmission system to prevent the coded test signal transmission system from transmitting the unique coded test signal at the one or more undetectable frequencies.

7. The system of claim 1, wherein one or both of the coded test signal transmission system and the coded test signal receiving system is configured to determine one or more avoided frequencies that are used by other systems along the route, and wherein the coded test signal transmission system is configured to avoid transmitting the coded test signal using the one or more avoided frequencies.

8. The system of claim 1, wherein the spread spectrum chirping coded signal includes a random signal.

9. The system of claim 1, wherein the coded test signal receiving system is configured to determine that the route is damaged in response to the unique coded test signal that is received by the coded test signal receiving system failing to meet a matching threshold.

10. A method comprising:
receiving a unique coded test signal transmitted by a coded test signal transmission system along a route at a coded test signal receiving system, wherein the receiving the unique coded test signal comprises receiving the unique coded test signal as a spread spectrum chirping coded signal including a random signal;
switching the spread spectrum chirping coded signal between on and off states;
changing the spread spectrum chirping coded signal each time the coded test signal transmission system switches the spread spectrum chirping coded signal to the on state; and
determining one or more characteristics of the route based, at least in part, on the unique coded test signal, wherein the receiving the unique coded test signal comprises receiving the unique coded test signal that is transmitted over at least two frequencies during a period of time, and wherein the method further comprises:
storing coded data at the coded test signal receiving system; and
comparing the unique coded test signal received by the coded test signal receiving system to the coded data.

11. The method of claim 10, further comprising:
determining one or more undetectable frequencies; and
preventing transmission of the unique coded test signal by the coded test signal transmission system at the one or more undetectable frequencies.

12. The method of claim 10, further comprising:
determining one or more avoided frequencies that are used by other systems along the route; and
avoiding transmission of the unique coded test signal using the one or more avoided frequencies.

13. The method of claim 10, wherein the determining the one or more unique characteristics comprises determining that the route is damaged in response to the received unique coded test signal failing to meet a matching threshold.

14. A system comprising:
a first sub-system configured to receive a unique coded test signal transmitted by a second sub-system along a route, wherein the unique coded test signal comprises a spread spectrum chirping coded signal, wherein the second sub-system is configured to switch the spread spectrum chirping coded signal between on and off states, wherein the second sub-system is configured to change the spread spectrum chirping coded signal each time the second sub-system switches the spread spectrum chirping coded signal to the on state, wherein the second sub-system transmits the unique coded test signal is over at least two frequencies during a period of time, and wherein the first sub-system is configured to store coded data that is compared to the unique coded test signal received by the first sub-system;
wherein at least one of:
the first sub-system is configured to determine one or more characteristics of the route based on the unique coded test signal as received by the first sub-system; or
the first sub-system is configured to communicate information about the unique coded test signal as received by the first sub-system to another sub-system that is not the first sub-system, for the another sub-system to determine the one or more characteristics of the route based on the information.

15. A system comprising:
a coded test signal transmission system configured to transmit a unique coded test signal along a route, wherein the unique coded test signal comprises a spread spectrum chirping coded signal, wherein the coded test signal transmission system is configured to switch the spread spectrum chirping coded signal between on and off states, and wherein the coded test signal transmission system is configured to change the spread spectrum chirping coded signal each time the coded test signal transmission system switches the spread spectrum chirping coded signal to the on state; and
a coded test signal receiving system configured to receive the unique coded test signal along the route,
wherein the unique coded test signal received by the coded test signal receiving system is used to determine one or more characteristics of the route,
wherein the coded test signal receiving system is configured to determine one or more undetectable frequencies, and wherein the coded test signal receiving system is configured to communicate with the coded test signal transmission system to prevent the coded test signal transmission system from transmitting the unique coded test signal at the one or more undetectable frequencies.

16. A system comprising:
a coded test signal transmission system configured to transmit a unique coded test signal along a route, wherein the unique coded test signal comprises a spread spectrum chirping coded signal, wherein the coded test signal transmission system is configured to switch the spread spectrum chirping coded signal between on and off states, and wherein the coded test signal transmission system is configured to change the spread spectrum chirping coded signal each time the coded test signal transmission system switches the spread spectrum chirping coded signal to the on state; and
a coded test signal receiving system configured to receive the unique coded test signal along the route,
wherein the unique coded test signal received by the coded test signal receiving system is used to determine one or more characteristics of the route,
wherein one or both of the coded test signal transmission system and the coded test signal receiving system is configured to determine one or more avoided frequencies that are used by other systems along the route, and wherein the coded test signal transmission system is configured to avoid transmitting the coded test signal using the one or more avoided frequencies.

17. A method comprising:
receiving a unique coded test signal transmitted by a coded test signal transmission system along a route at a coded test signal receiving system, wherein the receiving the unique coded test signal comprises receiving the unique coded test signal as a spread spectrum chirping coded signal including a random signal;
switching the spread spectrum chirping coded signal between on and off states;
changing the spread spectrum chirping coded signal each time the coded test signal transmission system switches the spread spectrum chirping coded signal to the on state;
determining one or more characteristics of the route based, at least in part, on the unique coded test signal;
determining one or more undetectable frequencies; and
preventing transmission of the unique coded test signal by the coded test signal transmission system at the one or more undetectable frequencies.

18. A method comprising:
receiving a unique coded test signal transmitted by a coded test signal transmission system along a route at a coded test signal receiving system, wherein the receiving the unique coded test signal comprises receiving the unique coded test signal as a spread spectrum chirping coded signal including a random signal;
switching the spread spectrum chirping coded signal between on and off states;
changing the spread spectrum chirping coded signal each time the coded test signal transmission system switches the spread spectrum chirping coded signal to the on state;
determining one or more characteristics of the route based, at least in part, on the unique coded test signal;
determining one or more avoided frequencies that are used by other systems along the route; and
avoiding transmission of the unique coded test signal using the one or more avoided frequencies.

\* \* \* \* \*